United States Patent [19]

Momany

[11] 4,228,158
[45] Oct. 14, 1980

[54] SYNTHETIC PEPTIDES HAVING PITUITARY GROWTH HORMONE RELEASING ACTIVITY

[75] Inventor: Frank A. Momany, Memphis, Tenn.
[73] Assignee: Beckman Instruments, Inc., Fullerton, Calif.
[21] Appl. No.: 25,553
[22] Filed: Mar. 30, 1979
[51] Int. Cl.² .................. A61K 37/00; C07C 103/52; C08L 37/00
[52] U.S. Cl. .................. 424/177; 260/112.5 R; 260/8
[58] Field of Search .................. 260/112.5 R, 8; 424/177

[56] References Cited
U.S. PATENT DOCUMENTS 3,479,333 11/1969 Grenen .................. 260/112.5 R OTHER PUBLICATIONS
Lien, et al., FEBS Letter 88, No. 2, 1978, 208–210.
White, et al., Principles of Biochem, 6th ed. 1308–1313.
Guyton, Medical Physiology, 5th ed. 988–1004.
Schally, et al., Science 179, 341–350.

*Primary Examiner*—Delbert R. Phillips
*Attorney, Agent, or Firm*—R. J. Steinmeyer; J. E. Vanderburgh; Robert S. Frieman

[57] ABSTRACT

Novel pentapeptides having the following amino acid sequence

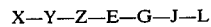

X—Y—Z—E—G—J—L wherein X is selected from a group consisting of —NH$_2$, —NHCH$_3$, and —N(CH$_3$)$_2$; Y and G are independently selected from a group consisting of tyrosine, tryptophan, and phenylalanine, Z and E are independently selected from a group consisting of D-tyrosine, D-tryptophan, and D-phenylalanine; J is selected from a group consisting of natural amino acids and the D-configuration thereof; and L is a C-terminal functional group selected from a group consisting of amide, amide lower alkyl, amide di(lower alkyl), lower alkoxy, hydroxy, and carboxy and the lower ester derivatives thereof; and the pharmaceutically acceptable salts thereof. These peptides act directly on the pituitary to release growth hormone therefrom.

16 Claims, No Drawings

SYNTHETIC PEPTIDES HAVING PITUITARY GROWTH HORMONE RELEASING ACTIVITY

BACKGROUND OF THE INVENTION

1. Field of the Invention

This invention relates to pentapeptides which possess pituitary growth hormone releasing activity.

2. Description of the Prior Art

Growth hormone, which is secreted from the pituitary, causes growth of all tissues of the body that are capable of growing. In addition, growth hormone is known to have the following basic effects on the metabolic process of the body:

1. Increased rate of protein synthesis in all cells of the body;
2. Decreased rate of carbohydrate utilization in cells of the body;
3. Increased mobilization of free fatty acids and use of fatty acids for energy.

A deficiency in growth hormone secretion can result in various medical disorders, such as some instances of dwarfism.

Various ways are known to release growth hormone. For example, chemicals such as argine, L-dihydroxyphenylamine (L-DOPA), glucagon, vasopressin, and insulin induced hypoglycemia, as well as activities such as sleep and exercise, indirectly cause growth hormone to be released from the pituitary by acting in some fashion on the hypothalmus perhaps either to decrease somatostatin secretion or to increase an unknown endogenous growth hormone-releasing hormone or both.

Compounds which directly act on the pituitary to release growth hormone include prostaglandin $E_1$ and $E_2$, theophylline, and cyclic nucleotides. However, these compounds neither specifically release growth hormone nor are they believed to act at the putative growth hormone-releasing hormone receptors in the peripheral membrane of the pituitary cell to initiate growth hormone release.

In addition, under special conditions certain chemically defined peptides, e.g., vasopressin, thyroid-releasing hormone (TRH), luteinizing hormone-releasing hormone (LH-RHL, α-melanocyte-stimulating hormone (α-MSH), glucagon, substance P, neurotensin; Met-enkephelin, β-endorphin, cholera-enderotoxin, and basic myelin protein, act to release growth hormone from the pituitary. However, only TRH acts directly on the pituitary to elicit this response. Furthermore, the above listed peptides release other pituitary hormones and under most experimental conditions do not release growth hormone. For example, TRH does not release growth hormone in normal rats or in normal humans or from pituitaries of normal rats or monkeys. In vitro, TRH releases growth hormone, prolactin, and thyroid stimulating hormone (TSH) and in vivo TRH releases these hormones from bovine pituitary.

Vasopressin's induced release of growth hormone is considered to be due to a non-specific response to stress caused by administration of high dosages of vasopressin.

Accordingly it would be highly desirable to have a compound which directly acts on the pituitary under normal experimental conditions to effect the release of growth hormone therefrom. Such peptides would be useful in vitro as unique research tools for understanding how growth hormone secretion is regulated at the pituitary level and would also be useful in vivo to treat symptoms related to growth hormone deficiencies.

SUMMARY OF THE INVENTION

In accordance with the present invention there is provided peptides which act directly on the pituitary under normal experimental conditions in vitro to release growth hormone therefrom.

These growth hormone releasing pentapeptides can be utilized in vitro as unique research tools for understanding, inter alia, how growth hormone secretion is regulated at the pituitary level.

Also, the growth hormone releasing pentapeptides of the instant invention can also be administered in vivo to increase growth hormone release.

More particularly, this invention encompasses novel peptides having the formula

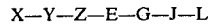

X—Y—Z—E—G—J—L wherein X is selected from a group consisting of —NH$_2$, -NHCH$_3$, and —N(CH$_3$)$_2$; Y and G are independently selected from a group consisting of tyrosine, tryptophan, and phenylalanine; Z and E are independently selected from a group consisting of D-tyrosine, D-tryptophan, and D-phenylalanine; J is selected from a group consisting of natural amino acids and the D-configuration thereof; and L is a C-terminal functional group selected from a group consisting of an amide, amide lower alkyl, amide di(lower alkyl), lower alkoxy, hydroxy, and carboxy and the lower ester derivatives thereof; and the pharmaceutically acceptable salts thereof.

DETAILED DESCRIPTION OF THE PREFERRED EMBODIMENTS

The pentapeptides of this invention have the amino acid sequence represented by formula I:

X—Y—Z—E—G—J—L       (I)

wherein X is selected from a group consisting of —NH$_2$, —NHCH$_3$, and —N(CH$_3$)$_2$; Y and G are amino acid residues independently selected from a group consisting of tyrosine, tryptophan, and phenylalanine; Z and E are independently selected from a group consisting of D-tyrosine, D-tryptophan, and D-phenylalanine; J is selected from a group consisting of natural amino acids and the D-configuration thereof; and L is a C-terminal functional group selected from a group consisting of amide (—CONH$_2$), amide lower alkyl (—NHR), amide di(lower alkyl) (—CONR$_1$R$_2$), lower alkoxy (—CH$_2$OR), hydroxy (—CH$_2$OH), carboxy (—COOH) and the lower ester derivatives thereof (—COOR) and the pharmaceutically acceptable salts thereof.

Preferably, the pentapeptides of this invention have the amino acid sequence represented by formula II:

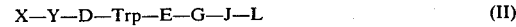

X—Y—D—Trp—E—G—J—L       (II)

wherein X, Y, and L are as defined above; E is selected from the group consisting of D-tryptophan and D-phenylalanine; G is selected from the group consisting of tryptophan and phenylalanine; and J is selected from the group consisting of methionine, D-methionine, leucine, D-leucine, phenylalanine, D-phenylalanine, arginine, D-arginine, proline, and D-proline.

All amino acid residues identified herein are in the natural or L-configuration unless otherwise specified.

Abbreviations for amino acid residue have been used in accordance with the following standard peptide nomenclature:

| Tyr | -L-tyrosine | Ile | -L-isoleucine |
|---|---|---|---|
| D-tyr | -D-tyrosine | D-Ile | -D-isoleucine |
| Gly | -glycine | Leu | -L-leucine |
| Phe | -L-phenylalanine | D-Leu | -D-leucine |
| D-Phe | -D-phenylalanine | Thr | -L-threonine |
| Met | -L-methionine | D-Thr | -D-threonine |
| D-Met | -D-methionine | Val | -L-valine |
| Ala | -L-alanine | D-Val | -D-valine |
| D-Ala | -D-alanine | Pro | -L-proline |
| Ser | -L-serine | D-Pro | -D-proline |
| D-Ser | -D-serine | Gln | -L-glutamine |
| Lys | -L-lysine | D-Gln | -D-glutamine |
| D-Lys | -D-lysine | Glu | -L-glutamic acid |
| Asn | -L-asparagine | D-Glu | -D-glutamic acid |
| D-Asn | -D-aspargine | Trp | -L-tryptophan |
| His | -L-histidine | D-Trp | -D-tryptophan |
| D-His | -D-histidine | D-Asp | -D-aspartic acid |
| Arg | -arginine | D-Arg | -D-arginine |

The term "pharmaceutically acceptable salts," as used herein, refers to the non-toxic alkali metal, alkaline earth metal and ammonium salts commonly used in the pharmaceutical industry including the sodium, potassium, lithium, calcium, magnesium, barium, ammonium and protamine zinc salts which are prepared by methods well known in the art. The term also includes non-toxic acid addition salts which are generally prepared by reacting the compounds of this invention with a suitable organic or inorganic acid. Representative salts include the hydrochloride, hydrobromide, sulfate, bisulfate, acetate, oxalate, valerate, oleate, laurate, borate, benzoate, lactate, phosphate, tosylate, citrate, maleate, fumarate, succinate, tartrate, napsylate, and the like.

The term "natural amino acids", as used herein, refers to the amino acids glycine, alanine, valine, leucine, isoleucine, proline, hydroxyproline, serine, threonine, cysteine, methionine, aspartic acid, glutamic acid, asparagine, glutamine, arginine, lysine, histidine, phenylalanine, tyrosine, and tryptophan.

The term "lower alkyl", as used herein, refers to straight and branched chain alkyl groups having from 1 to 6 carbon atoms, such as methyl, ethyl, n-propyl, iso-propyl, n-butyl, tert-butyl, sec-butyl, n-pentyl, n-hexyl, 1,2-dimethylbutyl, and the like. Preferably, the lower alkyl group is methyl or ethyl.

The term "lower alkoxy", as used herein, refers to straight and branched chain alkoxy groups having from 1 to 6 carbon atoms, such as methoxy, ethoxy, n-propoxy, iso-propoxy, n-butoxy, tert-butoxy, sec-butoxy, n-pentoxy, n-hexoxy, 1,2-dimethylbutoxy and the like. Preferably, the lower alkoxy group is methoxy or ethoxy.

The term "lower ester derivative", as used herein, refers to straight and branched chain alkyl ester derivatives having from 1 to 6 carbon atoms, such as methyl, ethyl, n-propyl, iso-propyl, n-butyl, tert-butyl, sec-butyl, n-pentyl, n-hexyl, and 1,2-dimethylbutyl ester derivatives and the like. Preferably, the lower ester derivative is a methyl ester derivative or an ethyl ester derivative.

Accordingly, each R, $R_1$, and $R_2$ is independently selected from a group consisting of straight and branched chain alkyl groups containing 1-6 carbon atoms. Preferably, each R, $R_1$, and $R_2$ are independently selected from the group consisting of alkyl group containing 1-2 carbon atoms.

Table I sets forth peptides within the scope of the instant invention.

TABLE I

X-Tyr-D-Trp-D-Trp-Trp-Met-L
X-Tyr-D-Trp-D-Trp-Trp-D-Met-L
X-Tyr-D-Trp-D-Trp-Trp-Leu-L
X-Tyr-D-Trp-D-Trp-Trp-D-Leu-L
X-Tyr-D-Trp-D-Trp-Trp-Phe-L
X-Tyr-D-Trp-D-Trp-Trp-D-Phe-L
X-Tyr-D-Trp-D-Trp-Trp-Arg-L
X-Tyr-D-Trp-D-Trp-Trp-D-Arg-L
X-Tyr-D-Trp-D-Trp-Trp-Pro-L
X-Tyr-D-Trp-D-Trp-Trp-D-Pro-L
X-Tyr-D-Trp-D-Trp-Phe-Met-L
X-Tyr-D-Trp-D-Trp-Phe-D-Met-L
X-Tyr-D-Trp-D-Trp-Phe-Leu-L
X-Tyr-D-Trp-D-Trp-Phe-D-Leu-L
X-Tyr-D-Trp-D-Trp-Phe-Phe-L
X-Tyr-D-Trp-D-Trp-Phe-D-Phe-L
X-Tyr-D-Trp-D-Trp-Phe-Arg-L
X-Tyr-D-Trp-D-Trp-Phe-D-Arg-L
X-Tyr-D-Trp-D-Trp-Phe-Pro-L
X-Tyr-D-Trp-D-Trp-Phe-D-Pro-L
X-Tyr-D-Trp-D-Phe-Trp-Met-L
X-Tyr-D-Trp-D-Phe-Trp-D-Met-L
X-Tyr-D-Trp-D-Phe-Trp-Leu-L
X-Tyr-D-Trp-D-Phe-Trp-D-Leu-L
X-Tyr-D-Trp-D-Phe-Trp-Phe-L
X-Tyr-D-Trp-D-Phe-Trp-D-Phe-L
X-Tyr-D-Trp-D-Phe-Trp-Arg-L
X-Tyr-D-Trp-D-Phe-Trp-D-Arg-L
X-Tyr-D-Trp-D-Phe-Trp-Pro-L
X-Tyr-D-Trp-D-Phe-Trp-D-Pro-L
X-Tyr-D-Trp-D-Phe-Phe-Met-L
X-Tyr-D-Trp-D-Phe-Phe-D-Met-L
X-Tyr-D-Trp-D-Phe-Phe-Leu-L
X-Tyr-D-Trp-D-Phe-Phe-D-Leu-L
X-Tyr-D-Trp-D-Phe-Phe-Phe-L
X-Tyr-D-Trp-D-Phe-Phe-D-Phe-L
X-Tyr-D-Trp-D-Phe-Phe-Arg-L
X-Tyr-D-Trp-D-Phe-Phe-D-Arg-L
X-Tyr-D-Trp-D-Phe-Phe-Pro-L
X-Tyr-D-Trp-D-Phe-Phe-D-Pro-L
X-Trp-D-Trp-D-Trp-Trp-Met-L
X-Trp-D-Trp-D-Trp-Trp-D-Met-L
X-Trp-D-Trp-D-Trp-Trp-Leu-L
X-Trp-D-Trp-D-Trp-Trp-D-Leu-L
X-Trp-D-Trp-D-Trp-Trp-Phe-L
X-Trp-D-Trp-D-Trp-Trp-D-Phe-L
X-Trp-D-Trp-D-Trp-Trp-Arg-L
X-Trp-D-Trp-D-Trp-Trp-D-Arg-L
X-Trp-D-Trp-D-Trp-Trp-Pro-L
X-Trp-D-Trp-D-Trp-Trp-D-Pro-L
X-Trp-D-Trp-D-Trp-Phe-Met-L
X-Trp-D-Trp-D-Trp-Phe-D-Met-L
X-Trp-D-Trp-D-Trp-Phe-Leu-L
X-Trp-D-Trp-D-Trp-Phe-D-Leu-L
X-Trp-D-Trp-D-Trp-Phe-Phe-L
X-Trp-D-Trp-D-Trp-Phe-D-Phe-L
X-Trp-D-Trp-D-Trp-Phe-Arg-L
X-Trp-D-Trp-D-Trp-Phe-D-Arg-L
X-Trp-D-Trp-D-Trp-Phe-Pro-L
X-Trp-D-Trp-D-Trp-Phe-D-Pro-L
X-Trp-D-Trp-D-Phe-Trp-Met-L
X-Trp-D-Trp-D-Phe-Trp-D-Met-L

X-Trp-D-Trp-D-Phe-Trp-Leu-L
X-Trp-D-Trp-D-Phe-Trp-D-Leu-L
X-Trp-D-Trp-D-Phe-Trp-Phe-L
X-Trp-D-Trp-D-Phe-Trp-D-Phe-L
X-Trp-D-Trp-D-Phe-Trp-Arg-L
X-Trp-D-Trp-D-Phe-Trp-D-Arg-L
X-Trp-D-Trp-D-Phe-Trp-Pro-L
X-Trp-D-Trp-D-Phe-Trp-D-Pro-L
X-Trp-D-Trp-D-Phe-Phe-Met-L
X-Trp-D-Trp-D-Phe-Phe-D-Met-L
X-Trp-D-Trp-D-Phe-Phe-Leu-L
X-Trp-D-Trp-D-Phe-Phe-D-Leu-L
X-Trp-D-Trp-D-Phe-Phe-Phe-L
X-Trp-D-Trp-D-Phe-Phe-D-Phe-L
X-Trp-D-Trp-D-Phe-Phe-Arg-L
X-Trp-D-Trp-D-Phe-Phe-D-Arg-L
X-Trp-D-Trp-D-Phe-Phe-Pro-L
X-Trp-D-Trp-D-Phe-Phe-D-Pro-L
X-Phe-D-Trp-D-Trp-Trp-Met-L
X-Phe-D-Trp-D-Trp-Trp-D-Met-L
X-Phe-D-Trp-D-Trp-Trp-Leu-L
X-Phe-D-Trp-D-Trp-Trp-D-Leu-L
X-Phe-D-Trp-D-Trp-Trp-Phe-L
X-Phe-D-Trp-D-Trp-Trp-D-Phe-L
X-Phe-D-Trp-D-Trp-Trp-Arg-L
X-Phe-D-Trp-D-Trp-Trp-D-Arg-L
X-Phe-D-Trp-D-Trp-Trp-Pro-L
X-Phe-D-Trp-D-Trp-Trp-D-Pro-L
X-Phe-D-Trp-D-Trp-Phe-Met-L
X-Phe-D-Trp-D-Trp-Phe-D-Met-L
X-Phe-D-Trp-D-Trp-Phe-Leu-L
X-Phe-D-Trp-D-Trp-Phe-D-Leu-L
X-Phe-D-Trp-D-Trp-Phe-Phe-L
X-Phe-D-Trp-D-Trp-Phe-D-Phe-L
X-Phe-D-Trp-D-Trp-Phe-Arg-L
X-Phe-D-Trp-D-Trp-Phe-D-Arg-L
X-Phe-D-Trp-D-Trp-Phe-Pro-L
X-Phe-D-Trp-D-Trp-Phe-D-Pro-L
X-Phe-D-Trp-D-Phe-Trp-Met-L
X-Phe-D-Trp-D-Phe-Trp-D-Met-L
X-Phe-D-Trp-D-Phe-Trp-Leu-L
X-Phe-D-Trp-D-Phe-Trp-D-Leu-L
X-Phe-D-Trp-D-Phe-Trp-Phe-L
X-Phe-D-Trp-D-Phe-Trp-D-Phe-L
X-Phe-D-Trp-D-Phe-Trp-Arg-L
X-Phe-D-Trp-D-Phe-Trp-D-Arg-L
X-Phe-D-Trp-D-Phe-Trp-Pro-L
X-Phe-D-Trp-D-Phe-Trp-D-Pro-L
X-Phe-D-Trp-D-Phe-Phe-Met-L
X-Phe-D-Trp-D-Phe-Phe-D-Met-L
X-Phe-D-Trp-D-Phe-Phe-Leu-L
X-Phe-D-Trp-D-Phe-Phe-D-Leu-L
X-Phe-D-Trp-D-Phe-Phe-Phe-L
X-Phe-D-Trp-D-Phe-Phe-D-Phe-L
X-Phe-D-Trp-D-Phe-Phe-Arg-L
X-Phe-D-Trp-D-Phe-Phe-D-Arg-L
X-Phe-D-Trp-D-Phe-Phe-Pro-L
X-Phe-D-Trp-D-Phe-Phe-D-Pro-L

The peptides of the instant invention can be prepared by classical methods known in the art or, preferably, by using standard solid-phase techniques. The synthesis is commenced from the C-terminal end of the peptide using an α-amino protected resin. A suitable starting material can be prepared, for instance, by attaching the required α-amino acid to a chloromethylated resin, a hydroxymethyl resin, or a benzhydrylamine resin. One such chloromethylated resin is sold under the trade-name BIO-BEADS SX-1 by Bio Rad Laboratories, Richmond, Calif. and the preparation of the hydroxymethyl resin is described by Bodonszky et al., *Chem. Ind.* (London) 38, 1597 (1966). The benzhydrylamine (BHA) resin has been described by Pietta and Marshall, *Chem. Commn.* 650 (1970) and is commercially available from Beckman Instruments, Inc., Palo Alto, Calif. in the hydrochloride form thereof (BHA.HCl).

In the preparation of the compounds of this invention, an α-amino protected amino acid is coupled to the chloromethylated resin with the aid of, for example, cesium bicarbonate catalyst, according to the method described by Gisin, *Helv. Chim. Acta*, 56, 1467 (1973). After the initial coupling, the α-amino protecting group is removed by a choice of reagents including trifluoroacetic acid (TFA) or hydrochloric acid (HCl) solutions in organic solvents at room temperature. After removal of the α-amino protecting group, the remaining protected amino acids are coupled stepwise in the desired order. Each protected amino acid is generally reacted in about a 3-fold excess using an appropriate carboxyl group activator such as dicyclohexylcarbodiimide (DCC) in solution, for example, in methylene chloride ($CH_2Cl_2$)-dimethylformamide (DMF) mixtures.

After the desired amino acid sequence has been completed, the desired peptide is decoupled from the resin support by treatment with a reagent such as hydrogen fluoride (HF) which not only cleaves the peptide from the resin, but also cleaves all remaining side-chain protecting groups. When the chloromethylated resin is used, hydrogen fluoride treatment results in the formation of the free peptide acids of Formula I (Y=—COOH). When the benzhydrylamine resin is used, hydrogen fluoride treatment results directly in the free peptide amides of Formula I (Y=—$CONH_2$). Alternatively, when the chloromethylated resin is employed, the side-chain protected peptide can be decoupled by treatment of the peptide-resin with ammonia to give the desired side-chain protected amide or with an alkylamine to give a side-chain protected alkylamide or dialkylamide. Side-chain protection is then removed in the usual fashion by treatment with hydrogen fluoride to give the free amides, alkylamides, or dialkylamides.

In preparing the esters of this invention the resins used to prepare the acids of Formula I (Y=—COOH) are employed and the side-chain protected peptide is cleaved with base and the appropriate alcohol, i.e., methanol. Side-chain protecting groups are then removed in the usual fashion by treatment with hydrogen fluoride to obtain the desired ester.

The solid-phase procedure discussed above is well known in the art and has been essentially described by J. M. Stewart, *Solid Phase Peptide Synthesis:* (Freeman and Co., San Francisco, 1969).

The growth hormone releasing pentapeptides of Formula I are useful in vitro as unique tools for understanding how growth hormone secretion is regulated at the pituitary level. This includes use in the evaluation of many factors thought or known to influence growth hormone secretion such as age, sex, nutritional factors, glucose, amino acids, fatty acids, as well as fasting and non-fasting states. In addition, the pentapeptide of this invention can be used in the evaluation of how other hormones modify growth hormone releasing activity. For example, it has already been established that somatostatin inhibits growth hormone release. Other hormones that are important and in need of study as to their effect on growth hormone release include the gonadal hormones testosterone, estradiol, and progesterone; the adrenal hormones cortisol and other corticoids, epinephrin and norepinephrine; the pancreatic and gastrointestine hormones, insulin, glucagon, gastric, secretion, the vasoactive intestinal peptides, i.e., bombesin; and the thyroid hormones thyroxine and triiodothyronine. The pentapeptides of Formula I can also be employed to investigate the possible negative or positive feedback effects of some of the pituitary hormones, e.g., growth hormone and endorphin peptides, on the pituitary to modify growth hormone release. Of particular scientific importance is the use of these pentapeptides to elucidate the subcellular mechanisms mediating the release of growth hormone.

The pentapeptides of Formula I can also be administered to warm blooded animals, including man, to release growth hormone in vivo. For example, the pentapeptides of Formula I can be administered to treat symptoms related to growth hormone deficiencies. In addition, these pentapeptides can be administered to commercially important animals to accelerate and increase their rate and extent of growth.

Accordingly, the present invention includes within its scope pharmaceutical compositions comprising, as an active ingredient, at least one of the compounds of Formula I in association with a pharmaceutical carrier or diluent. The compounds of this invention can be administered by oral, parenteral (intramuscular, intraperitoneal, intravenous (IV) or subcutaneous injection), nasal, vaginal, rectal or sublingual routes of administration and can be formulated in dosage forms appropriate for each route of administration.

Solid dosage forms for oral administration include capsules, tablets, pills, powders and granules. In such solid dosage forms, the active compound is admixed with at least one inert pharmaceutically acceptable carrier such as sucrose, lactose, or starch. Such dosage forms can also comprise, as is normal practice, additional substances other than inert diluents, e.g., lubricating agents such as magnesium stearate. In the case of capsules, tablets and pills, the dosage forms may also comprise buffering agents. Tablets and pills can additionally be prepared with enteric coatings.

Liquid dosage forms for oral administration include pharmaceutically acceptable emulsions, solutions, suspensions, syrups, the elixirs containing inert diluents commonly used in the art, such as water. Besides, such inert diluents, compositions can also include adjuvants, such as wetting agents, emulsifying and suspending agents, and sweetening, flavoring, and perfuming agents.

Preparations according to this invention for parental administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized by, for example, filtration through a bacteria-retaining filter, by incorporating sterilizing agents into the compositions, by irradiating the compositions, or by heating the compositions. They can also be manufactured in the form of sterile water, or some other sterile injectable medium immediately before use.

Compositions for rectal or vaginal administration are preferably suppositories which may contain, in addition to the active substance, excipients such as cocoa butter or a suppository wax.

Compositions for nasal or sublingual administration are also prepared with standard excipients well known in the art.

The dosage of active ingredient in the compositions of this invention may be varied; however, it is necessary that the amount of the active ingredient shall be such that a suitable dosage form is obtained. The selected dosage depends upon the desired therapeutic effect, on the route of administration, and on the duration of the treatment. Generally, dosage levels of between 0.001 to 10 mg/kg. of body weight daily are administered to mammals to obtain effective release of growth hormone.

The following examples are provided for the purpose of further illustration only and are not intended to be limitations on the disclosed invention.

EXAMPLE 1

Synthesis of $H_2N$-Tyr-D-Trp-D-Trp-Phe-Met-$CONH_2$

BHA.HCl resin was placed in a reaction vessel. The following procedure was then employed in conjunction with a Beckman brand Peptide Synthesizer Model No. 990 in preparing the pentapeptide $H_2N$-Tyr-D-Trp-D-Trp-Phe-Met-$CONH_2$:

1. Methylene chloride ($CH_2Cl_2$; about 10 ml/gm of BHA.HCl resin) was added to the reaction vessel. The BHA.HCl resin was washed with vigorous stirring for about 1.5 minutes. The $CH_2Cl_2$ solution was then drained from the reaction vessel. This washing step was repeated once.

2. A triethylamine solution (($Et_3N$)/$CH_2Cl_2$ (10:90); about 10 ml/gm BHA.HCl resin) was added to the washed BHA.HCl resin in the reaction vessel. The resulting mixture was vigorously stirred for about 1.5 minutes. The solution was then drained from the reaction vessel.

3. Another $Et_3N_3$/$CH_2Cl_2$ (10:90) solution (about 10 ml/gm BHA.HCl) was added to the reaction vessel. The BHA.HCl resin resin was neutralized by vigorous stirring for about 20 minutes. The solution was then drained from the reaction vessel.

4. $CH_2Cl_2$ (about 10 ml/gm of BHA.HCl resin) was added to the reaction vessel. The resulting mixture was vigorously stirred for about 1.5 minutes. The solution was then drained from the reaction vessel. This procedure was repeated an additional two times.

5. An 0.5 molar (M) dicyclohexylcarbodiimide (DCC) in $CH_2Cl_2$ solution (about 2.5 times the theoretical amount of total binding capacity of the BHA.HCl resin originally placed in the reaction vessel) was added to the reaction vessel. The resulting mixture was vigorously stirred for about 1.5 minutes. The solution was then drained from the reaction vessel.

6. Tertiarybutyloxycarbonyl-methionine (Boc-Met; about 2.5 times the theoretical amount of the total binding capacity of the BHA.HCl resin originally placed in the reaction vessel) in about 50 ml of a DMF-$CH_2Cl_2$ (5:45) solution was added to the reaction vessel. The resulting mixture was vigorously stirred until a negative ninhydrin test was obtained (about 120 minutes). The solution was then drained from the reaction vessel.

7. $CH_2Cl_2$ (about 10 ml/gm of BHA.HCl resin) was added to the reaction vessel. The resulting solution was vigorously stirred for about 1.5 minutes. The solution was then drained from the reaction vessel. This washing procedure was repeated once.

8. DMF (about 10 ml/gm of BHA.HCl resin) was added to the reaction vessel. The resulting mixture was stirred for about 1.5 minutes. The solution was then drained from the reaction vessel.

9. $CH_2Cl_2$ (about 10 ml/gm of BHA.HCl resin) was added to the reaction vessel. The resulting mixture was vigorously stirred for about 1.5 minutes. The solution was then drained from the reaction vessel. This washing procedure was repeated an additional two times.

10. A trifluoroacetic acid (TFA)/$CH_2Cl_2$ (40:60) solution (about 10 ml/gm of BHA.HCl resin) was added to the reaction vessel. The resulting mixture was vigorously stirred for about 1.5 minutes. The solution was then drained from the reaction vessel.

11. Another TFA/$CH_2Cl_2$ (40:60) solution (about 10 ml/gm of BHA.HCl resin) was added to the reaction vessel. The resulting mixture was vigorously stirred for about 20 minutes. The solution was then drained from the reaction vessel.

12. Chloroform ($CHCl_3$; about 10 ml/gm of BHA.HCl resin) was added to the reaction vessel. The resulting mixture was vigorously stirred for about 1.5 minutes. The solution was then drained from the reaction vessel.

13. An ethanol (EtOH)/$CH_2Cl_2$ (30:70) solution (about 10 ml/gm of BHA.HCl resin) was added to the reaction vessel. The resulting mixture was vigorously stirred for about 1.5 minutes. The solution was then drained from the reaction vessel. This washing step was repeated once.

Steps 1 through 13 were then repeated employing the following sequence of amino acids:

Boc-Phe
Boc-D-Trp
Boc-D-Trp
Boc-Tyr (BrZ*)

*BrZ denotes p-bromobenzyloxycarbonyl

After completion of the synthesis of the desired peptide resin, the reaction vessel containing the peptide resin was then placed in a dessicator and dried overnight under a vacuum. The dried peptide resin was removed from the reaction vessel and placed in another vessel suitable for HF cleavage. This latter vessel also contained a magnetic stirring bar. A quantity of anisol sufficient to wet the peptide resin was added to this vessel. The vessel was next connected to an HF line and placed under a vacuum to remove any air therein. The vessel was then cooled to about $-78°$ C. with a dry ice-acetone bath. Doubly distilled HF (about 10 ml/gm of peptide resin) was added to the vessel. The dry ice-acetone bath was then removed from the vessel and replaced by an ice-water bath. The vessel's contents were vigorously stirred for about 45 minutes while the vessel remained immersed in the ice-water bath. Most of the HF in the vessel was then removed by water aspiration. After the majority of HF was removed by water aspiration, the remaining HF and anisole were removed via a vacuum pump.

The vessel's contents were washed with about 100 ml of ether to further remove any residual anisole.

The peptide was removed from the resin by extraction with 30% aqueous acetic acid (aq.HOAc). The aq.HOAc was lypholized off to yield a fluffy peptide powder.

The peptide was then purified by partition chromatography employing a butonol:HOAc:water (4:1:5) system.

EXAMPLE 2

In Vitro Growth Hormone Release Study

Female rats of the CD-1 strain were housed in a constant temperature room at 24° C. with 14 hours light and 10 hours darkness. The rats were fed Purina brand rat chow ab libitum.

All studies were started between 0800 and 1000 hours.

Pituitaries were removed from 20 day old female rats. Two pituitaries were incubated at 36° C. in 1 ml of lactated Ringer's solution in 10 ml polytetrafluoroethylene beakers in a Dubnoff Shaker (90 cycles/min.). The pituitaries were incubated a total of 4 hours ($P_1$, $P_2$, $I_3$, and $I_4$). After two successive one hour preincubation periods ($P_1$, $P_2$), the peptide was added to the incubation medium hourly for 2 hours ($I_3$, $I_4$).

This in vitro study was performed in triplicate and a standard radioimmunoassay of growth hormone present in the incubation medium was performed in duplicate. The hormonal activity was calculated as the difference ($\Delta$) of growth hormone (GH) levels between $I_3$, $I_4$ and $P_2$, i.e., ($I_3-P_2$) and ($I_4-P_2$). P values were calculated by Students' t test using six growth hormone values for each value recorded.

The growth hormone radioimmunoassay reagents were distributed by the National Institute of Arthritis and Metabolite Disease Division (NIAMDD) program. The growth hormone values were calculated in terms of nanograms (ng) of a rat standard with a growth hormone potency of 0.61 units/mg. The results obtained are set forth in Table II.

TABLE II

| IN VITRO GROWTH HORMONE RELEASE[1,2] | | | | |
|---|---|---|---|---|
| Peptide | Control | 1μg | 20μg | 100μg |
| $H_2N$—Tyr—D-Trp—D-Trp—Phe—Met—$CONH_2$ | $-54 \pm 35$ | $1697 \pm 222$ | $1530 \pm 208$ | $219 \pm 113$[3] |

[1] Given in terms of ngΔGH/ml incubation medium ± standard error of the mean (SEM)
[2] P Value <0.001 unless otherwise noted
[3] P Value ~0.02

The results set forth in Table II demonstrate that peptides within the scope of the instant invention can induce a significant in vitro release of growth hormone from the pituitary.

By introducing various other hormones, e.g., somatostatin, testosterone, cortisol, insulin, etc., into the incubation medium of Example 2, one can study what effect these latter hormones have on the regulation of growth hormone secretion.

EXAMPLE 3

In Vivo Diagnostic Application

A peptide within the scope of this invention is injected IV into a mammal, including a human. Blood samples are taken before and at +15 minute intervals after the IV injection for about 1 to about 2 hours. Serum growth hormone levels are measured on each of the blood samples. The rise in growth hormone level is an index of the response. The degree of the growth hormone response is indicative of whether the hypothalmic-pituitary unit is functioning normally to secrete growth hormone.

This test can be employed for evaluating whether the hypothalamic-pituitary system is normal under a large number of different clinical and experimental conditions in both healthy and disease states. The test has application at all ages and in both sexes.

Based on this disclosure, many other modifications and ramifications will naturally suggest themselves to those skilled in the art. These are intended to be comprehended as within the scope of this invention.

The embodiments of the invention in which an exclusive property or privilege is claimed are defined as follows:

1. A peptide having a formula

X-Y-Z-E-G-J-L and the pharmaceutically acceptable non-toxic acid addition salts thereof wherein
X is selected from a group consisting of —NH$_2$, —NHCH$_3$, and —N(CH$_3$)$_2$;
Y and G are independently selected from a group consisting of Tyr, Trp, and Phe;
Z and E are independently selected from a group consisting of D-Tyr, D-Trp, and D-Phe;
J is selected from a group consisting of Leu, Ile, and Met; and
L is selected from a group consisting of —CONH$_2$, —CONHR, —CONR$_1$R$_2$, —CH$_2$OR, —CH$_2$OH, —COOH, and —COOR, wherein
each R, R$_1$, and R$_2$ is independently selected from a group consisting of straight and branched alkyl groups containing 1-6 carbon atoms.

2. The peptide of claim 1 of the formula

H$_2$N-Tyr-D-Trp-D-Trp-Phe-Met-CONH$_2$.

3. The peptide of claim 1 wherein each R, R$_1$, and R$_2$ is independently selected from the group consisting of alkyl groups containing 1-2 carbon atoms.

4. The peptide of claim 1 wherein L is —CONH$_2$.

5. A method of releasing growth hormone from a pituitary comprising contacting said pituitary with the peptide of claims 2 or 4.

6. The peptide of claim 1 of the formula

H$_2$N-Tyr-D-Trp-D-D-Trp-Phe-J-L.

7. The peptide of claim 1 wherein each R, R$_1$, and R$_2$ is independently selected from the group consisting of alkyl groups containing 1-2 carbon atoms.

8. The peptide of claim 1 wherein L is —CONH$_2$.

9. The peptide of claim 6 wherein each R, R$_1$, and R$_2$ is independently selected from the group consisting of alkyl groups containing 1-2 carbon atoms.

10. The peptide of claim 6 wherein L is —CONH$_2$.

11. A compound of the formula

Boc-Tyr(BrZ)-D-Trp-D-Trp-Phe-Met-  ® wherein
BrZ is p-bromobenzyloxycarbonyl;
Boc is t-butyloxycarbonyl; and
® is benzhydrylamine resin.

12. A method of releasing growth hormone from a pituitary comprising contacting said pituitary with the peptide of claim 1 wherein L is —CONH$_2$.

13. A method of releasing growth hormone from a pituitary comprising contacting said pituitary with the peptide of claim 9.

14. A method of releasing growth hormone from a pituitary comprising contacting said pituitary with the peptide of claim 1 wherein L is —CONH$_2$.

15. A method of releasing growth hormone from a pituitary comprising contacting said pituitary with the peptide of claim 6.

16. A method of releasing growth hormone from a pituitary comprising contacting said pituitary with the peptide of claim 6 wherein L is —CONH$_2$.

* * * * *